United States Patent [19]
Flitsch et al.

[11] Patent Number: 5,627,271
[45] Date of Patent: May 6, 1997

[54] GLYCOLIPIDS, THEIR PREPARATION AND USE

[75] Inventors: Sabine L. Flitsch, Oxford, United Kingdom; Benedicte Guilbert, Saint-Renan, France

[73] Assignee: Genzyme Limited, Haverhill, United Kingdom

[21] Appl. No.: 318,758

[22] PCT Filed: Apr. 1, 1993

[86] PCT No.: PCT/GB93/00687

§ 371 Date: Oct. 13, 1994

§ 102(e) Date: Oct. 13, 1994

[87] PCT Pub. No.: WO93/20226

PCT Pub. Date: Oct. 14, 1993

[30] Foreign Application Priority Data

Apr. 1, 1992 [GB] United Kingdom ............... 9207182

[51] Int. Cl.$^6$ ............... C07G 3/00; A61K 38/51; C12N 9/10
[52] U.S. Cl. ............... 536/18.5; 424/94.5; 435/193
[58] Field of Search ............... 536/18.5; 424/94.5; 435/193

[56] References Cited

FOREIGN PATENT DOCUMENTS 0212400  3/1987  European Pat. Off. ......... C07H 15/10
WO9116449  10/1991  WIPO ............... C12P 21/100

OTHER PUBLICATIONS

Zimmerman, P. et al. (1988) "Azidosphingosine Glycosylation in Glycosphingolipid Synthesis" *J. Carbohydrate Chemistry*, & (2):435–452.

Nicolaou, K. et al. (1988) "A Practical and Enantioselective Synthesis of Glycosphingolipids and Related Compounds. Total Synthesis of Globotriaosylceramide (GB3)" *J. Am. Chem. Soc.*, 110:7910–7912.

Yu, R. et al. (1976) "In Vitro Biosynthesis of Sialosylgalacto–sylceramide (G7) by Mouse Brain Microsomes" *The Journal of Biological Chemistry*, 251(1):196–203.

Graf, L. et al. (1974) "Serological Activity of Glycosphingolipids: Effects of Chain Length of the Fatty acid Residue in Cytolipin H" *Chemistry and Physics of Lipids*, 13:367–371.

*Primary Examiner*—John W. Rollins
*Attorney, Agent, or Firm*—William G. Gosz

[57] ABSTRACT

A process for preparing a glycolipid of formula (I): $[(sac)_{m+n}]$—O—$CH_2$—CHX—CH(OQ)—Y wherein Q is H or a blocking group; X is $N_3$ or $NH_2$; Y is a lipid residue; each sac is a saccharide; and m and n are each integers; comprises reacting a corresponding glycolipid of formula (II): $(sac)_n$—O—$CH_2$—CHX—CH(OQ)—Y with the corresponding saccharide $(sac)_m$ or a reactive derivative thereof, in the presence of an enzyme that catalyses the reaction. Compounds of formulae (I) and (II) are suitable for elaboration to a variety of saccharide ceramides.

13 Claims, No Drawings

5,627,271

GLYCOLIPIDS, THEIR PREPARATION AND USE

FIELD OF THE INVENTION

This invention relates to glycolipids and to their preparation and use.

BACKGROUND OF THE INVENTION

Glycolipids are compounds of importance in therapy. In particular, glycosphingolipids are naturally-occurring compounds found in the membranes of all animal cells and in some plant cells. One such compound is cytolipin H, a pure lipid hapten, which has been isolated from human epidermoid carcinoma extracts.

Cytolipin H is N-lignoceroyl-1-sphingosyl lactoside. This is a compound of formula I (see formulae below) when Q is H, X is —NH—CO—$C_{23}H_{47}$, Y is —CH=CH—$C_{13}H_{27}$ and $(sac)_{m+n}$ is a lactose residue. A synthesis of such compounds is reported by Nicolaou et al, JACS (1988) 110: 7910–7912, and comprises coupling a protected di- or trisaccharide with a protected sphingosine azide which is then elaborated.

Yu et al, J. Biol. Chem. (1976) 251(1): 198–203, discloses that a sialyltransferase in mouse brain microsomes catalyses the synthesis of sialosylgalactosylceramide from added galactocerebroside and CMP-NANA. The product, i.e. NeuNAc($\alpha$,2-3)gal($\beta$,1-1) cer, and the substrate, are compounds of formulae I and II in which X is —NH—CO—$C_{12}H_{25}$ and Y is —CH=CH—$C_{13}H_{27}$. The enzymatic activity is apparently dependent on the ceramide structure of the glycolipids.

Products of the ceramide type, i.e. containing two hydrophobic residues, have serological activity that depends on the nature of Y; see Graf et al, Chemistry and Physics of Lipids (1974) 13: 367–371.

EP-A-0212400 discloses a chemical synthesis of compounds of formula II wherein n=1, sac is glucopyranose, X is —NH—CO—($C_{14-24}$ alkyl) and Y is —CH=CH—$C_{13}H_{27}$ or an analogous group. Intermediates in this synthesis are of the same structure except that X is $N_3$ or $NH_2$. The latter is suitable for elaboration to a variety of groups X.

Zimmermann et al, J. Carbohydrate Chem. 7(2): 435–452 (1988), disclose similar compounds, and also analogous compounds wherein n=2. For example, in order to prepare lactosylceramide, the per-O-acetylated trichloroacetimidate of lactose is first coupled with a hydroxysphingosineazide-;the product is reduced and elaborated.

SUMMARY OF THE INVENTION

The present invention is based on the discovery that a glycolipid of the type obtained by coupling a saccharide and a sphingosine, but not a ceramide, i.e. X is $N_3$ or $NH_2$, is a satisfactory substrate for an enzymatic saccharide coupling reaction.

The substrate has formula II (preferably the natural configuration shown below), i.e.

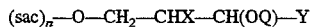

The product has formula I (preferably the natural configuration shown below), i.e.

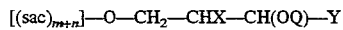

Many of the products and substrates are new. The advantage of using the new procedure to make glycolipids having at least two sugar moieties is that, except for elaboration to give any desired group X, the more expensive enzymatic reactions are conducted after the chemical modifications, giving greater efficiency and higher yields, as well as preserving the desired stereochemistry. The elaborated products are known compounds, or may be new compounds having properties analogous or perhaps superior to the related known compounds.

DESCRIPTION OF THE INVENTION

In the starting glycolipid (II), n is preferably 1 or 2. m is usually one, so that the novel process is used to add one sugar moiety at a time. If a glycolipid (II) in which n=1 is used as starting material, and many such compounds can be prepared by generally known techniques, the process of the invention can be repeated as many times as necessary to give a glycolipid having the desired number of sugar moieties.

The enzyme that is used in the invention is typically of the type that is known for the biosynthesis of N-linked sugars in glycoproteins. It is surprising that such known enzymes will also utilise glycolipids (II) as a substrate but, as is evident from the data herein, that is the case. Suitable sialyltransferases ($\alpha$2-3 and $\alpha$2-6) may be obtained from porcine or rat liver, and galactosyltransferase (from bovine milk, 2.4.1.22) and fucosyltransferase activity can also be used. Specific examples of enzymes that may be used are Gal$\beta$1, 3GalNAc-$\alpha$2, 3-sialyltransferase (EC 2.4.99.4) and Gal$\beta$1, 4GlcNAc-$\alpha$2, 6-sialyltransferase (EC 2.4.99.1).

Suitable substrates for the enzymes may be determined by routine experiment, but it is preferred, for example, that a glycolipid (II) to be coupled with sialyltransferase is a N-acetylglucosamine compound. $(sac)_n$ itself may also be a substrate, or acceptor, for the enzyme.

In the present invention, the glycolipid (II) is the "acceptor" molecule for the reaction. It is preferably prepared for reaction as a dispersion in a suitable medium, e.g. using a detergent and, if necessary or desired in order to keep and maintain a homogeneous system, sonication.

The other substrate of the reaction, i.e. $(sac)_m$, is preferably in the form of a reactive derivative known per se. Examples of such derivatives are nucleotide sugars, e.g. CMP-NANA, UDP-Gal and GDP-fucose.

Y is suitably an a-unsaturated long-chain alkyl group, e.g. of 10 to 24 C atoms. Examples are given in EP-A-0212400. Y is preferably a sphingosine group.

Both the starting materials, i.e. the glycolipid (II) and $(sac)_n$ are known compounds or can be prepared by known methods, e.g. as described in the prior art discussed above. See also Chart A, below, where the first four steps are given by way of illustration since compound (37) is known.

In and by the process of the invention, glycolipids of formulae I and II are generally prepared first as azides, i.e. in which X is $N_3$. Q may then be a blocking group, and other susceptible groups, e.g. in $(sac)_n$, may also be blocked. Many suitable blocking groups are known, as are procedures for their introduction and removal. Q is, for example, benzoyl.

Compounds of formula I or II in which X is $N_3$ may be converted to the corresponding amine by known techniques. Examples of suitable reducing conditions are given below. Any blocking group(s) may be removed at any suitable stage.

Novel compounds of formulae I and II include those having the following characteristics:

(i) a terminal fucose or other alkylsaccharide residue, e.g. as shown in Chart D;

(ii) a LeX head group, an example of which is again the product of Chart D;

(iii) the sugar adjacent to the lipid group includes NHAc, e.g. as shown in Charts A to D; and (iv) a terminal sialic acid group, e.g. as shown in Chart B.

The compounds of formula I are useful for preparing cytolipin H and other corresponding glycolipids in which X is, say, acylamino, by known elaboration techniques. This need be the only post-enzymatic chemical reaction, to obtain useful glycolipids, by virtue of this invention.

The following Examples illustrate compounds and processes of the invention, and also how the starting materials may be prepared and the products used. Reference should be made to the Charts, below, for the formulae of the compounds identified in the Examples by reference numerals.

EXAMPLE 1 (Chart A)

Compound (38): A solution of (37) (143 mg, 0.23 mmol, 1 eq) and (2) (100 mg, 0.23 mmol, 1.0 eq) in 14 ml of dry dichloromethane, with molecular sieves powder 4A was cooled to −20° C., and 260 µl (26 µmol) of 0.1M trifluoroboron etherate ($CH_2Cl_2$ solution) was added. The reaction mixture was stirred for 10 min, diluted with 20 ml petroleum ether 40–60, and washed with 10 ml sat. $NaHCO_3$. The organic fraction was filtered, dried over $Na_2SO_4$ and concentrated in vacuo. The residue was chromatographed in petroleum ether 40–60/ethyl acetate (3:1) leading to white crystals (185 mg, 94%). Rf=0.6 in petroleum ether 40–60/ethyl acetate (1:1). $^1$H NMR ($CDCl_3$, 500 MHz) δ/ppm: 0.89 (3H, t, J 7.0, —$(CH_2)_2$—C$\underline{H}$), 1.23–1.21 (22H, m, —(C$\underline{H}$)$_{11}$—$CH_3$), 1.88 (3H, s, —$COCH_3$), 1.93–1.99 (2H, m, —C$\underline{H}$=CH—$CH_2$—), 2.04 and 2.08 (6H, 2s, 2x —$COCH_3$), 3.62 (1H, dd, J 4.6, 9.9, —$OCH_2$—(1H)), 3.82–3.89 (3H, m, C(5)H, —$OCH_2$—(1H), —$CHN_3$—), 4.17 (1H, dd, J 2.4, 12.3, C(6)H), 4.28 (1H, dd, J 4.7, C(6)H'), 4.38 (1H, dd, J 8.5, 10.7, C(2)H), 5.19 (1H, dd, J 9.1, 10.1, C(4)H), 5.42–5.49 (3H, m, C(1)H, —C$\underline{H}_B$=$CH_A$—$C_{13}H_{27}$, —CHOBz), 5.71–5.78 (1H, m, —CH$_B$=C$\underline{H}_A$—$C_{13}H_{27}$), 5.79 (1H, dd, C(3)H), 7.42–8.01 (9H, m, $C_6H_4$, —OBz).

Compound (26): Compound (38) (183 mg, 0.21 mmol) was dissolved in 7 ml 95% ethanol and 6.1 ml of 99% hydrazine monohydrate was added. The solution was stirred for 45 min at 70°–75° C. and the volatile products were removed in vacuo. The oily residue was redissolved three times in 2 ml ethanol and concentrated in vacuo, leading to a white powder of the 2-amino compound which was used with no further purification in the following step.

To a suspension of crude product of the previous step in 24 ml pyridine, 12 ml of acetic anhydride was added under argon. The solution was stirred for 1 h at 70°–80° C., concentrated in vacuo and chromatographed on silica (petroleum ether 40–60/ethyl acetate (2:3)). The resulting oil was dissolved in methanol and water added, leading to the precipitation of (26). The white powder was collected by filtration, washed carefully with water and dried in vacuo. (118 mg, 78%). Rf=0.5 in petroleum ether/ethyl acetate 1:2. $^1$H NMR ($CDCl_3$, 500 MHz) δ/ppm: 0.89 (3H, t, J 7.0, —$(CH_2)_{11}$—C$\underline{H}_3$), 1.27–1.40 (22H, m, —(C$\underline{H}_2)_{11}$—$CH_3$), 1.96–2.10 (17H, m, 5x—$COCH_3$, —CH=CH—C$\underline{H}_2$), 3.61 (1H, dd, J 5.0, —$OCH_2$—$CN_3$—), 3.67–3.75 (3H, m, C(5)H, —$N_3$CH—, C(2)H), 3.85 (1H, dd, J 10.6, 6.6, —$OCH_2$—$CN_3$—), 4.14–4.18 (1H, m, C(6)H), 4.26 (1H, dd, J 12.3, 4.8, C(6)H'), 4.87 (1H, d, J 8.2, C(1)H), 5.04–5.08 (1H, m, C(4)H), 5.33 (1H, dd, J 8.1, 4.7, =CH—C$\underline{H}$OAc), 5.40–5.46 (2H, m, —C$\underline{H}_B$=$CH_A$—$CH_2$—, C(3)H), 5.53 (1H, d, J 8.3, NH), 5.80 (1H, dt, J 15.3, 6.7, —CH$_B$=C$\underline{H}_A$—$CH_2$). M.S. (DCl):MH+=697. M.S. (FAB):M.W.+M.W.$_{Na}$=719. I.R. ($CHCl_3$) ν/cm$^{-1}$: 2104 (—$N_3$).

Compound (17): Under dry inert conditions, 580 µl (232 µmol) of 0.4M sodium methoxide was added to a solution of (26) (408 mg, 586 µmol) in 18 ml of methanol. The solution was stirred at room temperature for 2.5 h, then neutralised with ion-exchange resin (IR-120 (H$^+$)), filtered and concentrated in vacuo, leading to (27) as a white residue (306 mg, 99%). Rf=0.65 in $MeOH/CHCl_3/H_2O$ 12:12.3. $^1$H NMR (DMSO, 500 MHz) δ/ppm: 0.86 (3H, t, J 6.9, —$(CH_2)_{11}$—C$\underline{H}_3$), 1.24–1.33 (22H, m, —(C$\underline{H}_2)_{11}$—$CH_3$), 1.80 (3H, s, —$COCH_3$), 1.98–2.03 (2H, m, —HC=CH—C$\underline{H}_2$), 3.08 (1H, m, C(4)H), 3.22–3.53 (6H, m, —$N_3$CH—, C(5)H, C(6)H, C(2)H, $N_3$C—COH, C(3)H), 3.64–3.70 (3H, m, —$OCH_2$—$CN_3$, C(6)H'), 4.02 (1H, dd, =CH—C$\underline{H}$OH), 4.32 (1H, d, J 8.4, C(1)H), 4.49 (1H, t, J 5.6, C(6)—OH), 4.89 (1H, d, J 5.0 C(4)—OH), 4.97 (1H, s, C(4)—OH), 5.22 (1H, d, J 4.7, =CH—CHO$\underline{H}$—), 5.41 (1H, dd, J 7.0—C$\underline{H}_B$=$CH_A$—$CH_2$—), 5.63 (1H, dt, J 15.4, 6.7, —CH$_B$=C$\underline{H}_A$—$CH_2$—), 7.67 (1H, d, J 8.8, NH). M.S. (DCI) :MH$^+$=529.

EXAMPLE 2 (Chart B)

Compound (28): The acceptor (27) (16.5 mg, 31.2 µmol) was sonicated carefully for 15 min in 39 µl of 40 mM $MnCl_2$, 93 µl of 50 mM $NaN_3$, 102 µl and 330 µl of sodium cacodylate buffer pH 7.4 100 mM and 50 mM respectively. Then 35 µl of 2% BSA, 5.5 µl (5.5 U) of 1 U/µl calf intestinal alkaline phosphatase, 143 µl (1.92 U) of 6.7 U/500 µl UDP-Glc 4—epimerase, 29 µl (487 mU) of 8.4 U/500 µl galactosyl-transferase and 21.9 mg (37.9 µmol, 1.2 eq.) of UDP-Glc were added. The final concentrations were as follows: [Acceptor]=40 mM, [UDP-Glc]=49 mM, [$MnCl_2$] =2 mM, [$NAN_3$]=6 mM, [Sodium cacodylate]=50 mM.

The reaction mixture was incubated for 18 h at 37° C. then diluted to 3 ml with water and loaded on a reverse-phase column (Sorbsil C200 silica gel RP18, packed in methanol, washed with water). The column was carefully washed with water and the product (28) eluted with methanol. The organic fraction was concentrated in vacuo leading to a white product (18.7 mg, 87%). Rf=0.1 in chloroform/methanol 3:1. $^1$H NMR ($CD_3OD$, 500 MHz) δ/ppm: 0.89 (3H, t, J 7.0, —$(CH_2)_{11}$—C$\underline{H}_3$, 1.28–1.41 (22H, m, —(C$\underline{H}_2)_{11}$—$CH_3$, 1.97 (3H, s, —$COCH_3$), 2.05–2.09 (2H, m, CH$_B$=$CH_A$—C$\underline{H}_2$) 4.38 (1H, d, J 7.5, C(1)H), 4.47 (1H, d, J 8.3, C'(1)H), 5.49 (1H, dd, J 7.6, —C$\underline{H}_B$=$CH_A$—$CH_2$—), 5.74 (1H, dt, J 15.4, —CH$_B$=C$\underline{H}_A$—$CH_2$—). M.S. (ES$^+$):MNa$^+$=713.3.

Compound (29): (28) (5.4 mg, 7.8 µmol) was sonicated for 20 min in 65 µl of 10% Triton CF-54 and 600 µl of 10 mM sodium cacodylate buffer pH 7.4. Then 156 µl of 50 mM $NAN_3$, 65 µl of 2% BSA, 3.1 µl (3.1 U) of 1 U/µl CIAP, 48 µl (96 mU) of 2 mU/µl sialyltransferase and 5.3 mg (8.3 µmol) of CMP-NANA in 310 µl of 10 mM sodium cacodylate buffer pH 7.4 were added. The reaction mixture was adjusted to 1.3 ml with 47 µl of water and incubated at 37° C. for three days. The reaction mixture was loaded on a reverse-phase column (Sorbsil C200 silica gel RP18, packed in methanol, washed with water) which was washed with water. The sialylated compound (29) and the unreacted acceptor (28) were eluted with methanol/water (8:2) then methanol respectively. After concentration in vacuo (29) was obtained as a white residue. Rf=0.4 in chloroform/methanol/water (5:4:1). $^1$H NMR (500 MHz, $CD_3OD$) δ 0.90 (3H, t, J 7.0 Hz, —$(CH_2)_{12}CH_3$), 1.29–1.41 (22H, m, —(C$\underline{H}_2)_{11}CH_3$), 1.67 (1H, t, J 12.0 Hz, H$_{3a}$), 1.98 and 1.99

(2×3H, 2s, 2×COCH$_3$), 2.03–2.09 (2H, m, —CH=CHCH$_2$—), 2.77 (1H, q, J 4.7, 12 Hz, H$_{3e}$), 4.32 (1H,d, J 7.5 Hz, C(1)H), 4.64 (1H, d, J 8.4 Hz, C'(1)H), 5.48 (1H, ddt, J 1.3, 7.5, 15.4 Hz, —CH=CHC$_{13}$H$_{27}$), 5.74 (1H, dt, J 6.9, 14.6 Hz, —CH=CHC$_{13}$H$_{27}$) MS(FAB): (M+Na)$^+$=1004.

EXAMPLE 3 (Chart 3)

Compound (39): Compound (27) (40 mg, 75.7 µmol) was dissolved in 500 µl of methanol and 25.6 mg (113.5 µmol) of tin chloride dihydrate was added. The reaction mixture was stirred at room temperature for 22 h then reduced in vacuo, leading to a white powder which was chromatographed twice on silica in MeOH/CHCl$_3$/H$_2$O 4:5:1 giving (39) as an amorphous powder (26.1 mg, 69%). M.S.(ES$^+$):MH$^+$=503.5.

Compound (40): Compound (27) (10 mg, 18.3 µmol) was dissolved in 200 µl of methanol, and 6.4 mg of tin chloride dihydrate was added. The reaction mixture was stirred at room temperature for 22 h then reduced in vacuo. The residue was dissolved in 300 µl of a 50% CH$_3$CO$_2$Na solution, and 7.3 mg (18.9 µmol) of tetracosanoyl chloride in 300 µl of tetrahydrofuran was added. The reaction mixture was stirred vigorously at room temperature for 2 h, then reduced in vacuo. The white residue was washed with water, dried, then dissolved in warm methanol. The solution was cooled, leading to white crystals of (40) which were collected and dried in vacuo (8.2 mg, 51%). M.S. (FAB$^+$):MNa$^+$=876.

Compounds (41) and (42) may be prepared in analogous manner. (41) may also be prepared by the procedure of the following Example.

The GlcNAc ceramide (40) has been tested as a substrate for the galactosyltransferase with and without the addition of the detergent Triton CF-54. No conversion was obtained. Thus (40), as opposed to (27), does not get galactosylated by the transferase.

EXAMPLE 4

Compound (41): The acceptor (39) was dissolved in 37.4 µl of 40 mM MnCl$_2$, 90 µl of 50 mM NaN$_3$, 133 µl and 481 µl of respectively 100 mM and 50 mM sodium cacodylate buffer pH 7.4. To the solution were added 0.7 mg of BSA, 20.7 mg (35.8 µmol) of UDP-Glc, 5.3 µl of CiAP (1 U/µl), 1.1 U of galactosyltransferase and 2.7 U of UDP-Glc 4-epimerase. The reaction mixture was incubated at 37° C. for 24 h. The gel formed was loaded on a small reverse-phase column (Sorbisil C200 silica gel RP18, packed in methanol, washed with water). The column was washed with water and the product eluted with methanol. The organic fraction was reduced in vacuo leading to (41) as an amorphous powder contaminated with a trace of (39) (16.9 mg, 85%). M.S.(ES$^+$):MH$^+$=664.

(41) may be a substrate for sialyltransferase, and can be reacted in the presence of that enzyme with CMP-NANA.

EXAMPLE 5

Various glycolipids have been incubated with α2-3 and α2-6 sialyltransferases (from porcine and rat liver) in the presence of radio-labelled CMP-NANA. Table 1 shows the percentage yields of incorporation of radio-labelled CMP-NANA into the glycolipid acceptors of formula III. The results show good yields when (i) the azido-sphingosine lipid chain is present and (ii) N-acetyllactosamine is the lipid head group. Other glycolipids could accept NANA, but in relatively low yields.

The α2-3 sialyltransferase (from porcine liver; normally uses Gal-GalNAc as an acceptor substrate) did not catalyse any transfer to the new synthetic substrates. However, this transferase should be able to use glycolipid (54) as an acceptor. Lactosylceramide (x=16 and probably other values) is not an acceptor substrate.

TABLE 1

| Acceptor | R$_1$ | R$_2$ | Acceptor conc. (mM) | α2-6 ST yield (%)$^a$ | α2-3ST yield (%) |
|---|---|---|---|---|---|
| (20) | OH | N$_3$ | 6 | 2.4 (1.1) | |
| | | | | 2.6 (1.2) | |
| | | | 12 | 2.9 (1.1) | |
| | | | | 2.8 (1.3) | |
| | | | 50 | 5.9 (1.0) | |
| | | | | 8.3 (1.2) | |
| | | | 100 | 8.4 (1.0) | 2.5 |
| | | | | 9.5 (1.4) | |
| (1) | OH | —NH$_2$ | 12 | 4.1 (1.7) | 1.5 |
| | | | | 3.2 (1.3) | |
| | | | 100 | 4.1 (1.1) | 2.4 |
| | | | | 7.2 (1.5) | 2.5 |
| (28) | NHA$_c$ | —N$_3$ | 6 | 22.2 (1.5) | 1.1 |
| | | | 12 | 23.2 (1.5) | |
| | | | 50 | 47.0 (1.2) | |
| | | | 100 | 59.8 (1.8) | 1.5 |
| | | | | | 1.2 |
| lactosyl-ceramide | OH | —NHCO—(CH$_2$)$_x$CH$_3$ | 43 | 2.7 | |

$^a$numbers in brackets correspond to background values

EXAMPLE 6 (Chart D)

The acceptor (28) was tested as a substrate for α1-3 fucosyl transferase VI, by incubation with the enzyme and radio-labelled GDP-[$^{14}$C]fucose. The reaction conditions were: 45 mM Mes pH 6.5; 27 µM GDP-Fuc; 0.1% BSA; 0.1 mM NaCl; 5 mM MnCl$_2$; 5 mM MgCl$_2$; incubation at 37° C.). The reaction mixture was passed through a Sep-Pak C18 cartridge which was washed with 0.2M NaCl to ensure separation of all hydrophilic material. The lipid fraction was then eluted with MeOH. The incorporation of radioactivity into lipids was measured by scintillation counting.

In a first experiment, the transfer was monitored with time, using 0.2 mM (28) and 0.1 mU fucosyltransferase/100 µl incubation, and compared to a control incubation containing no acceptor. The results clearly showed incorporation of label into lipid above background. In a further experiment, but using 0.5 mU fucosyl transferase over 1 hour, the transfer of fucose was measured at 0.2, 1, 5 and 24 mM concentrations of (28). The percentage of fucose transferred was respectively about 50%, 60%, 65% and 70%.

Competition experiments were also carried out, using 0.2 mM acceptor (28), in the presence of various concentrations (0 to 2 mM) of N-acetyllactosamine which is a known substrate for the enzyme. The samples were analysed as before, for incorporation of fucose into lipid. The results indicate that the respective substrates are similarly good acceptors for the enzyme.

The radio-labelled product resulting from the incubation of (28) and GDP-*Fuc with the fucosyltransferase VI, was incubated with the α-L-fucosidase from beef kidney (E.C. 3.2.1.51). The reaction conditions comprised: c. 76 pmol [26000 cpm) of the glycolipid in 50 µl of 100 mM sodium citrate pH 5.0 containing 2 mg/ml of sodium taurocholate were incubated with 20 µl (80 mU) of α-L-fucosidase for 4.5 days at 25° C.; blank (24000 cpm): the α-L-fucosidase was replaced with 20 µl of 3.2 M ammonium sulphate. The assays were analysed as described before.

The results show that most of the radioactivity was recovered in the aqueous fraction whereas in the control it was in the organic fraction containing the glycolipid. This demonstrated that the hydrophilic fucose was cleaved by the α-L-fucosidase, confirming the α-linkage between the fucose and the N-acetyllactosaminyl carbohydrate.
Formulae
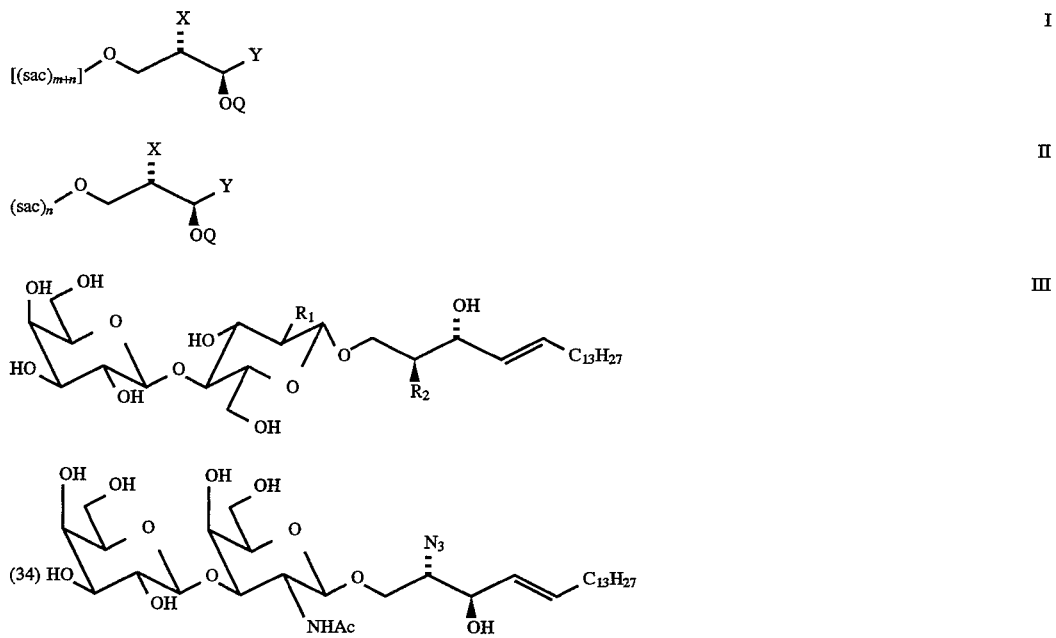
Chart A
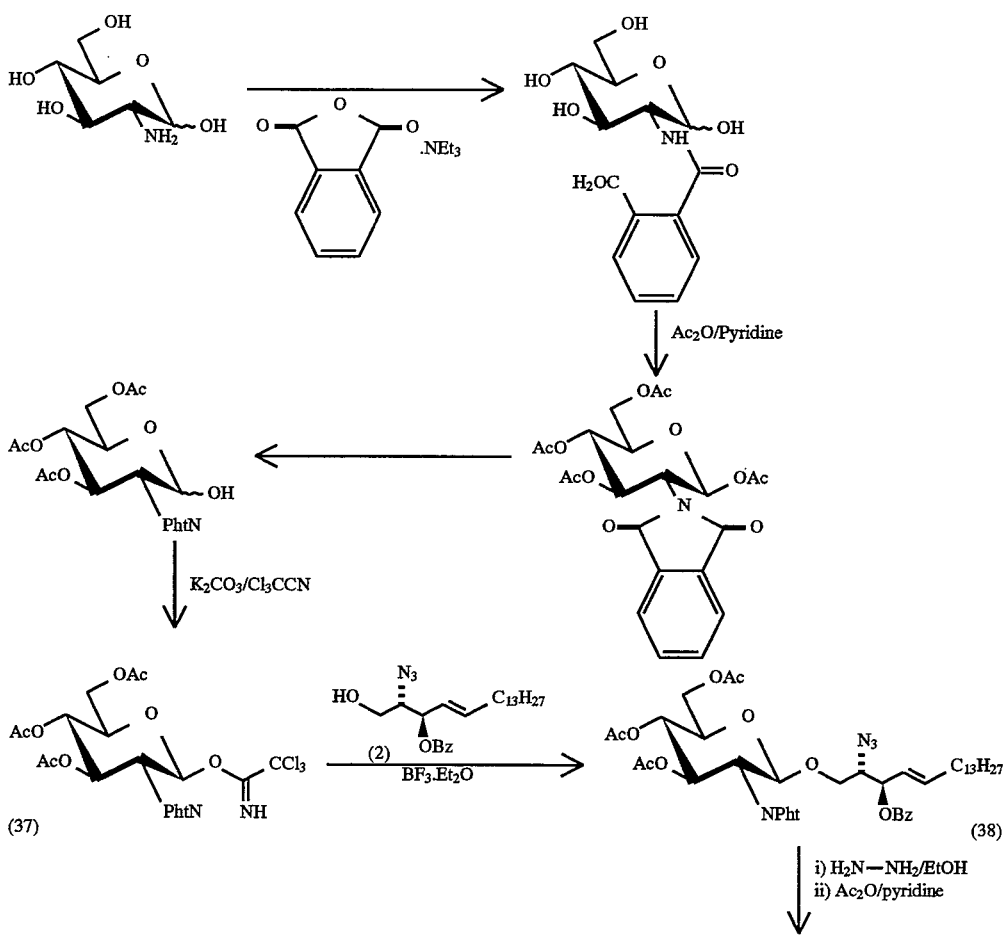

-continued
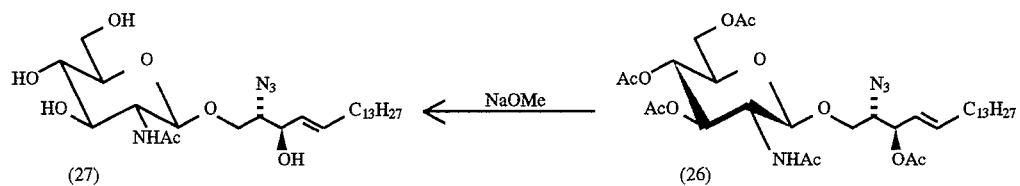
Chart B
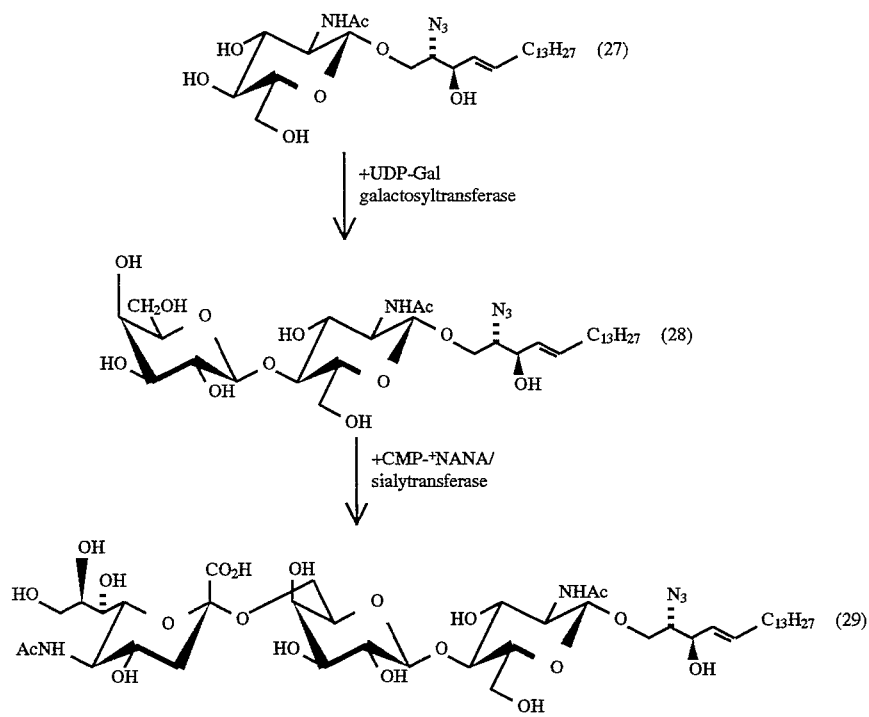
Chart C
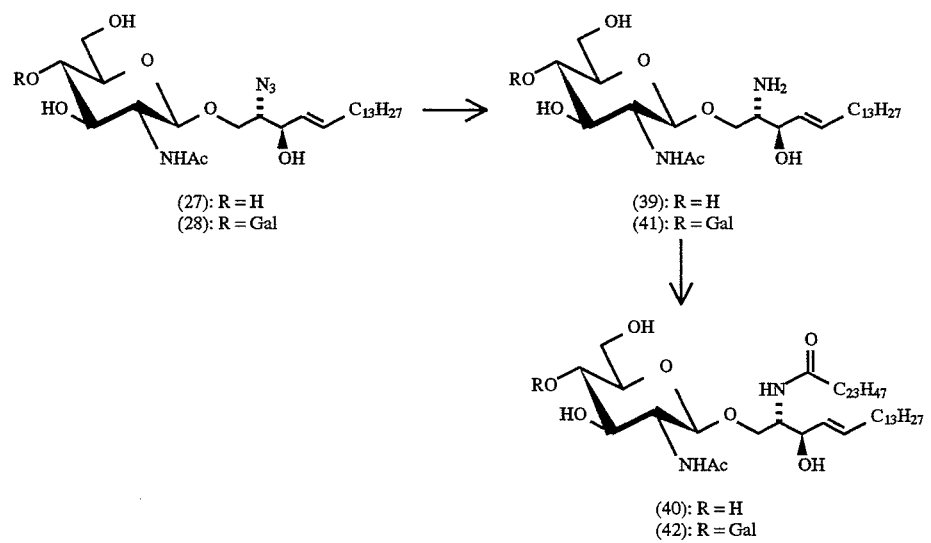

-continued
Chart D

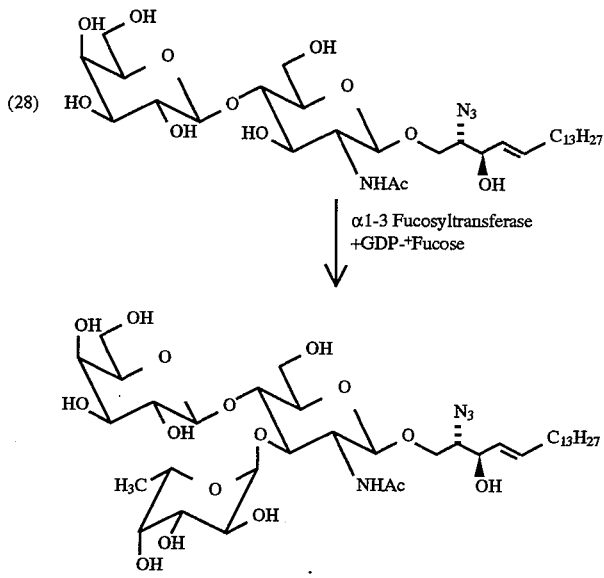

We claim:

1. A process for preparing a glycolipid of formula I $$[(sac)_{m+n}]-O-CH_2-CHX-CH(OQ)-Y$$

wherein Q is H or a blocking group; X is $N_3$ or $NH_2$; Y is a lipid residue; each sac is a saccharide; and m and n are each integers; which comprises reacting a corresponding glycolipid of formula II $$(sac)_n-O-CH_2-CHX-CH(OQ)-Y$$

with the corresponding saccharide $(sac)_n$ or a reactive derivative thereof, in the presence of an enzyme that catalyses the reaction.

2. A process according to claim 1, wherein Q is H.

3. A process according to claim 1 or claim 2, wherein m and n are each 1 or 2.

4. A process according to claim 3, wherein m is 1.

5. A process according to claim 4, wherein the corresponding saccharide is galactose, sialic acid or fucose.

6. A process according to claim 1, wherein Y is an α-unsaturated long-chain alkyl group.

7. A process according to claim 6, wherein Y is $-CH=CH-(CH_2)_{12}-CH_3$.

8. A process according to claim 1, wherein the glycolipids are in natural configuration.

9. A process according to claim 1, wherein the reactive derivative is a nucleotide sugar.

10. A glycolipid of formula I or II as defined in claim 1, which comprises a terminal fucose or other alkylsaccharide.

11. A glycolipid of formula I or II as defined in claim 1, which comprises a LeX head group.

12. A glycolipid of formula I or II as defined in claim 1, which comprises a terminal sialic acid.

13. A glycolipid of formula I or II as defined in claim 1, which comprises a NHAc-substituted saccharide adjacent to the lipid group.

* * * * *